US006867857B2

(12) United States Patent
Hobbs

(10) Patent No.: US 6,867,857 B2
(45) Date of Patent: Mar. 15, 2005

(54) FLOW CELL FOR OPTICAL ANALYSIS OF A FLUID

(75) Inventor: Steven E. Hobbs, West Hills, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/282,392

(22) Filed: Oct. 29, 2002

(65) Prior Publication Data

US 2004/0080744 A1 Apr. 29, 2004

(51) Int. Cl.$^7$ .......................... G01N 7/10; G01N 21/05
(52) U.S. Cl. .................. 356/246; 250/295.95; 422/68.1
(58) Field of Search ................................ 356/244, 246, 356/72–73, 36–42, 410, 411, 213; 250/295.95, 227.25; 422/50, 58, 68.1; 385/12, 125

(56) References Cited

U.S. PATENT DOCUMENTS

| 3,740,158 | A | * | 6/1973 | Bellinger et al. ........... 356/246 |
|---|---|---|---|---|
| 3,954,341 | A | * | 5/1976 | Uffenheimer ............... 356/410 |
| 4,019,372 | A | * | 4/1977 | Parkell et al. ............. 73/61.57 |
| 4,634,574 | A | * | 1/1987 | Spurlin et al. ................ 422/52 |
| 4,747,687 | A | * | 5/1988 | Hoppe et al. ............... 356/246 |
| 4,823,168 | A | | 4/1989 | Kamahori et al. .......... 356/246 |
| 4,908,112 | A | | 3/1990 | Pace ....................... 204/299 R |
| 4,989,974 | A | | 2/1991 | Anton et al. ................ 356/246 |
| 5,073,345 | A | * | 12/1991 | Scott et al. .................... 422/70 |
| 5,408,313 | A | | 4/1995 | Ponstingl et al. ........... 356/246 |
| 5,423,513 | A | * | 6/1995 | Chervet et al. ........ 250/227.25 |
| 5,444,807 | A | * | 8/1995 | Liu ............................. 385/125 |
| 5,599,503 | A | | 2/1997 | Manz et al. .............. 422/82.05 |
| 5,757,482 | A | | 5/1998 | Fuchs et al. ................ 356/246 |
| 5,815,258 | A | | 9/1998 | Nakanishi ................... 356/246 |
| 5,949,536 | A | * | 9/1999 | Mark ......................... 356/246 |
| 6,188,813 | B1 | | 2/2001 | Dourdeville et al. .......... 385/12 |
| 6,222,619 | B1 | * | 4/2001 | Herron et al. ................ 356/39 |
| 6,289,149 | B1 | * | 9/2001 | Druy et al. .................... 385/31 |
| 6,307,204 | B1 | | 10/2001 | Kanomata et al. .......... 250/373 |
| 6,444,474 | B1 | * | 9/2002 | Thomas et al. ............. 436/146 |
| 6,452,673 | B1 | * | 9/2002 | Leveille et al. ............. 356/246 |
| 6,542,231 | B1 | * | 4/2003 | Garrett ....................... 356/246 |
| 6,618,144 | B1 | * | 9/2003 | Reed .......................... 356/343 |
| 6,623,860 | B2 | * | 9/2003 | Hu et al. .................. 428/411.1 |

FOREIGN PATENT DOCUMENTS

EP        0 107 631        6/1983        ............ G01N/5/08

OTHER PUBLICATIONS

God, Ralf, et al., "Using multiparallel HPLC for purification in drug discovery from nature," Web document published at: http://www.iscpubs.com/articles/aln/n0112god.pdf, 2003 International Scientific Communications, Inc.

Waters Corporation brochure entitled "Waters 2488 Multi-channel UV/VIS Detector," World Wide Web document downloaded from http://www.waters.com/watersdivision/waters_website /Products/2488bro.pdf, Apr. 2001.

* cited by examiner

Primary Examiner—Gregory J. Toatley, Jr.
Assistant Examiner—Sang H. Nguyen
(74) Attorney, Agent, or Firm—Vincent K. Gustafson; Michael F. Labbee

(57) ABSTRACT

A flow cell for performing optical analysis of a fluid is provided. The flow cell comprises a monolithic cell housing that defines a detection chamber, fluid inlet and outlet ports and illumination and detection ports. Optical fibers are inserted in the illumination and detection ports, thereby forming substantially fluid-tight seals. A flow cell may be press-fit against a microfluidic device, with fluid sealing aided by O-rings.

32 Claims, 5 Drawing Sheets

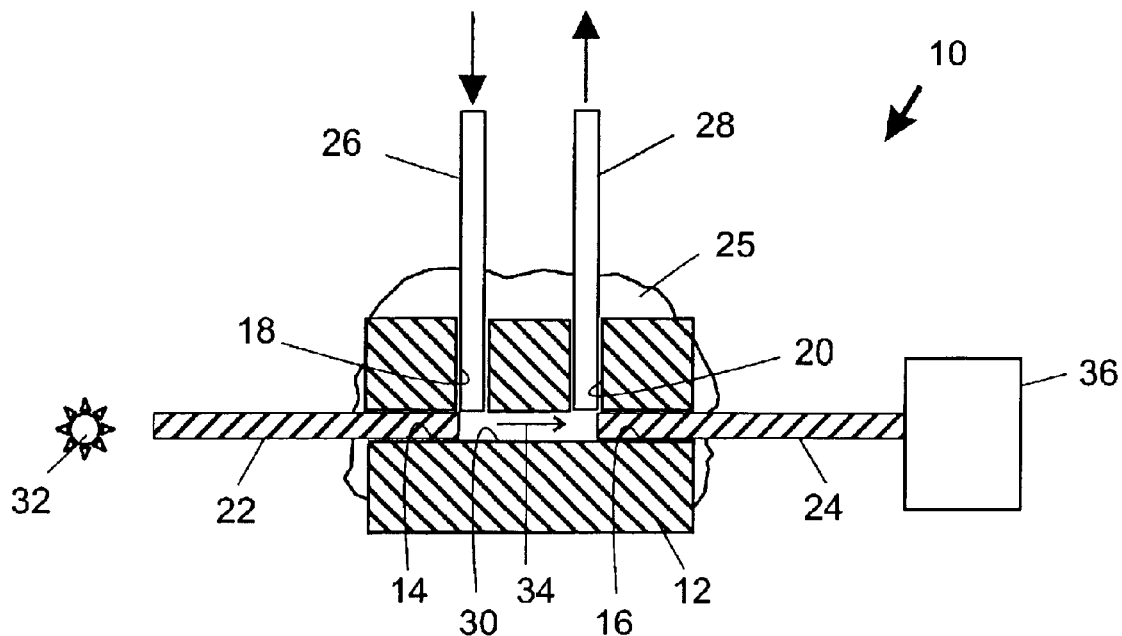
FIG._1
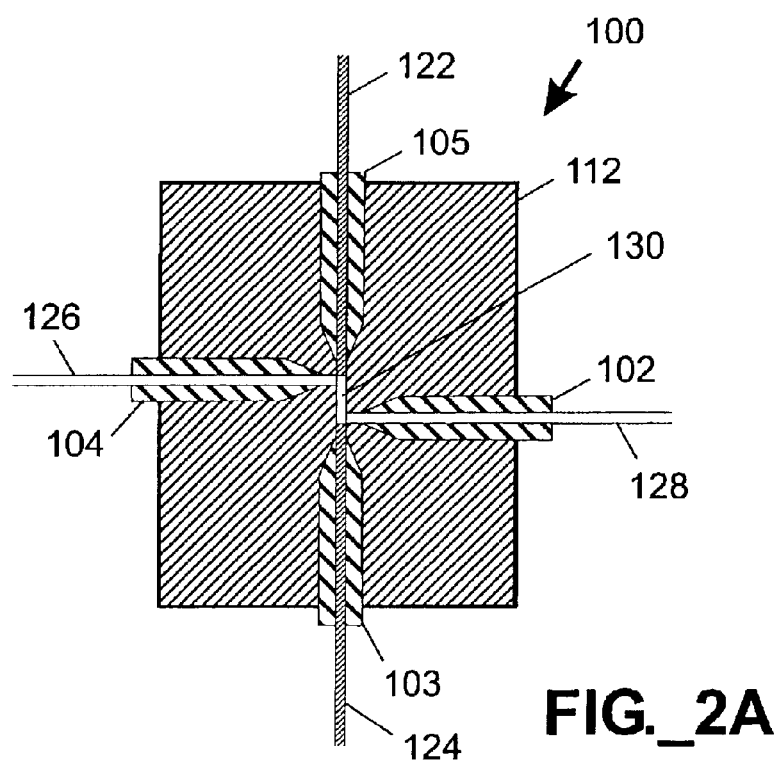
FIG._2A

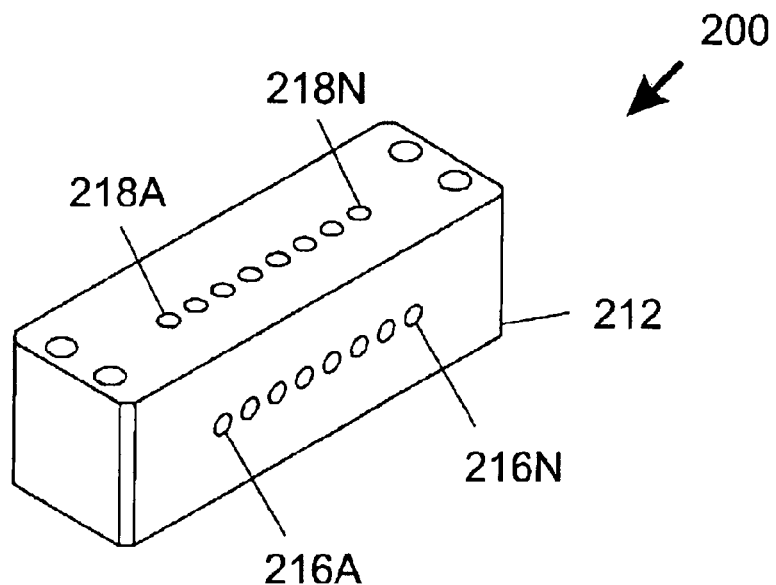
FIG._3A
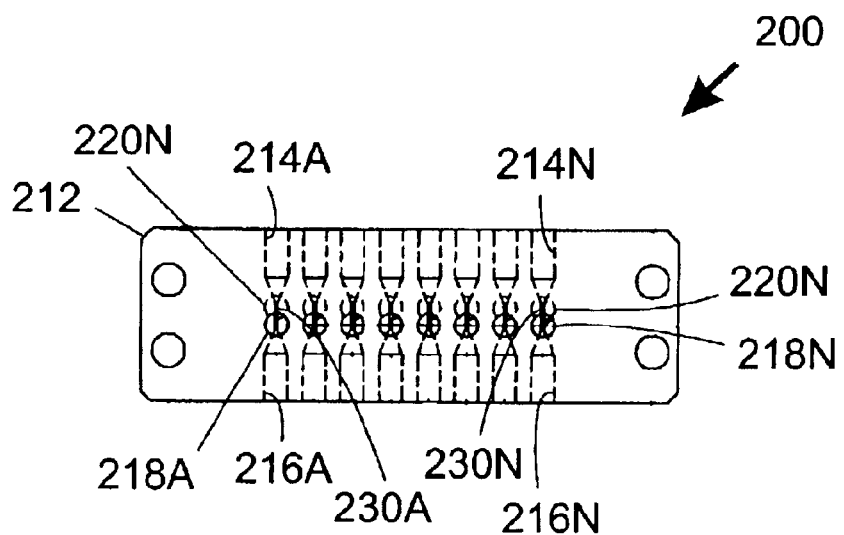
FIG._3B

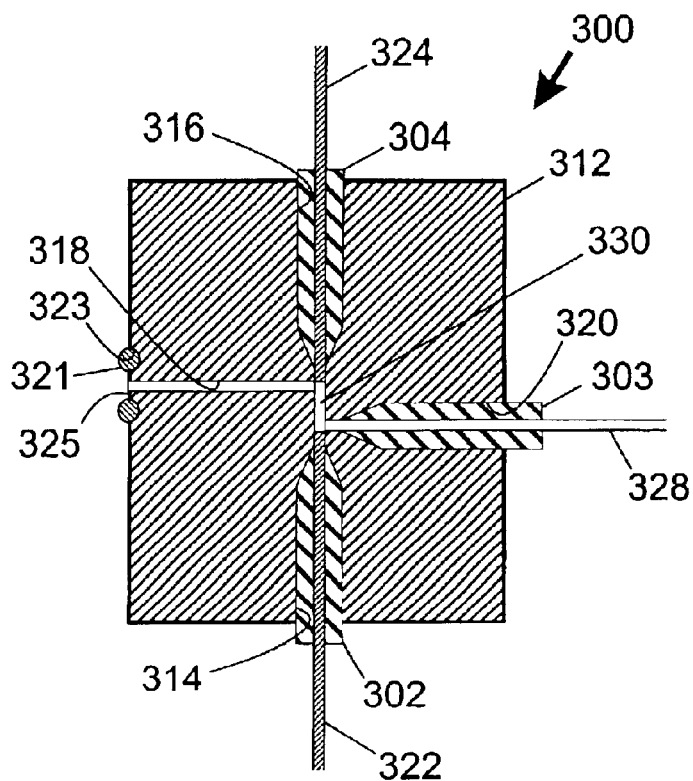
FIG._4A
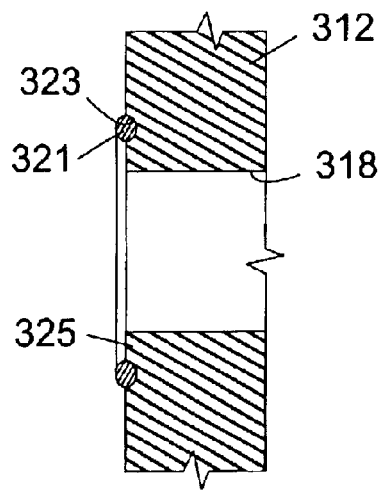
FIG._4B

FLOW CELL FOR OPTICAL ANALYSIS OF A FLUID

FIELD OF THE INVENTION

The present invention relates to systems for performing optical analysis of the output of one or more chromatography columns.

BACKGROUND OF THE INVENTION

There has been a growing interest in the manufacture and use of microfluidic systems for the acquisition of chemical and biological information. In particular, when conducted in microfluidic volumes, complicated biochemical reactions may be carried out using very small volumes of liquid. Among other benefits, microfluidic systems improve the response time of reactions, minimize sample volume, and lower reagent consumption. When volatile or hazardous materials are used or generated, performing reactions in microfluidic volumes also enhances safety and reduces disposal quantities.

One useful analytical process that may be performed using microfluidic devices is chromatography—a process routinely performed in various industrial and academic settings. Chromatography encompasses a number of methods that are used for separating closely related components of mixtures. In fact, chromatography has many applications including separation, identification, purification, and quantification of compounds within various mixtures. Chromatography is a physical method of separation wherein components partition between two phases: a stationary phase and a mobile phase. Samples are carried by a mobile phase through a bed of stationary phase and separated into their constituent components. Typically, the effluent from the separation column will be subjected to one or more analytical processes, including, but not limited to, optical detection, such as ultraviolet/visible light absorbance.

In order for optical analysis to yield useful results, an optical path transparent to the frequency of the illumination source must be provided. Moreover, the optical path must pass through a sufficient depth of the fluid being analyzed to provide a clear signal. Typical microfluidic devices may limit the ability to provide either of these desirable qualities for a number of reasons. For instance, many of the materials used to fabricate microfluidic devices, such as silicon, PEEK, and polyimide, may be opaque to or otherwise interfere with the transmission of desirable illumination frequencies, such as visible or ultraviolet light. Also, the dimensions of typical microfluidic conduits are such that any light path passing the depth or width of the conduit passes through a very small amount of fluid, thereby limiting the amount of information that may be acquired therefrom.

One proposed solution is to provide a microfluidic conduit with a path that provides an optical detection path along a length (as a opposed to a width or depth) of the fluid conduit, as disclosed in U.S. Pat. No. 5,757,482 to Fuchs et al. ("Fuchs") and U.S. Pat. No. 4,823,168 to Kamahori et al. ("Kamahori"). Fuchs discloses a micro-machined conduit extending vertically through a substrate that is the sandwiched between optically transmissive layers, providing a usefully long optical path length for optical detection of analytes. Kamahori discloses a cell body assemble from two etched halves that form a "Z"-shaped channel, bounded on either end with optically transmissive windows to provide an optical path through a length of the fluid channel. Both the Fuchs and Kamahori devices are limited, however, in that multiple components must be assembled to fabricate the device. In addition to adding complex and time-consuming assembly procedures (for example, to ensure precise alignment of the components), the bonding together of such components may require the use of adhesives that might contaminate the analyte stream. To the extent that adhesiveless bonding methods may be used, such methods are typically complex, often requiring substantial surface treatment of one or more of the components to facilitate bonding of dissimilar materials.

Thus, it would be desirable to provide a device for performing optical detection of analytes in a fluid stream that minimizes the number of components used to fabricate the device, is simple to manufacture, and provides the desired optical transmission through an optical path length that is substantially longer than the depth or width of a microfluidic channel.

SUMMARY OF THE INVENTION

In one aspect of the present invention, an optical analysis flow cell comprises a monolithic cell housing. The monolithic cell housing defines a detection chamber having a first end and a second end and a central axis; a fluid inlet port in fluid communication with the detection chamber; a fluid outlet port in fluid communication with the detection chamber; an illumination port in fluid communication with the detection chamber; and a detection port in fluid communication with the detection chamber. The illumination port is positioned at the first end of the detection chamber and the detection port is positioned at the second end of the detection chamber so that an optical path between the illumination port and the detection port traverses substantially all of the central axis.

In another separate aspect of the present invention, an optical analysis flow cell comprises a monolithic cell housing; a fluid inlet conduit sealingly affixed to and partially penetrating the monolithic cell housing, the fluid inlet conduit having an inner diameter; a fluid outlet conduit sealingly affixed to and partially penetrating the monolithic cell housing, the fluid outlet conduit having an inner diameter and the fluid outlet conduit being in fluid communication with the fluid inlet conduit; an illumination optical fiber sealingly affixed to and partially penetrating the monolithic cell housing, the source optical fiber being in fluid communication with the fluid inlet conduit and the fluid outlet conduit; and a detection optical fiber sealingly affixed to and partially penetrating the monolithic cell housing, the detection optical fiber being in fluid communication with the fluid inlet conduit, the fluid outlet conduit, and the illumination optical fiber. The illumination optical fiber and the detection optical fiber are in sensory communication over an optical path length that is substantially longer than the inner diameter of the fluid inlet conduit and substantially longer than the inner diameter of the fluid outlet conduit.

In another separate aspect of the present invention, an optical analysis flow cell comprises a monolithic cell housing defining a fluid flow channel having an orthogonal detection region, the orthogonal detection region having a detection axis; an optical signal fiber in sensory and fluid communication with the orthogonal detection region; and an optical detection fiber in sensory and fluid communication with the optical signal source across the detection axis. The optical signal fiber and the optical detection fiber are adapted to create a substantially fluid tight seal with the orthogonal detection region.

In another separate aspect of the invention, a system for performing optical analysis of a fluid sample comprises a flow cell having a plurality of inlet ports and a microfluidic device having a plurality of outlet ports. Each inlet port is adapted to form a press-fit seal with a corresponding outlet port.

In another separate aspect, any of the foregoing aspects may be combined for additional advantage.

These and other aspects and advantages of the invention will be apparent to the skilled artisan upon review of the following description, drawings and claims.

BRIEF DESCRIPTION OF THE DRAWINGS

FIG. 1 is a cross-sectional view of an optical detection flow cell according to a first embodiment.

FIG. 2A is a cross-sectional view of an optical detection flow cell according to a second embodiment.

FIG. 3A is a perspective view of an optical detection flow cell according to a third embodiment, the flow cell having a plurality of detection chambers.

FIG. 3B is a top view of the flow cell of FIG. 3A, showing the internal structures in ghosted lines.

FIG. 4A is a cross-sectional view of an optical detection flow cell according to a third embodiment.

FIG. 4B is a cross-sectional view of a portion of the optical detection flow cell of FIG. 4A.

DETAILED DESCRIPTION OF PREFERRED EMBODIMENTS OF THE INVENTION

Definitions

Figure 2B:
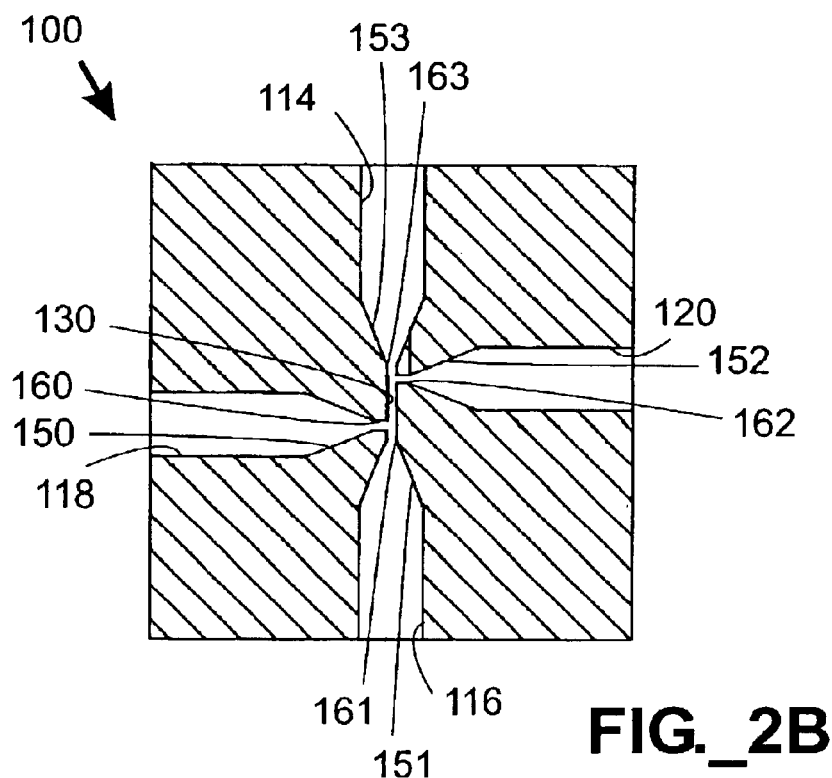
FIG. 2B is a cross-sectional view of the cell housing of the optical detection flow cell of FIG. 2A.

The term "microfluidic" as used herein refers to structures or devices through which one or more fluids are capable of being passed or directed and having at least one dimension less than about 500 microns.

The term "monolithic" as used herein refers to the property of being formed of a single piece, without requiring joints or seams.

Preferred Embodiments

Referring to FIG. 1, an optical detection flow cell 10 according to a first embodiment includes a monolithic cell housing 12, an illumination port 14, a detection port 16, a fluid inlet port 18, and a fluid outlet port 20. The cell housing may be made from a block of any suitable material, including, but not limited to, metals, such as aluminum or stainless steel; glasses; and polymers, such as poly(ether ether ketone) (PEEK) or polyimide. It will be readily apparent to one skilled in the art that the material may be selected to simplify manufacturing and/or minimize undesirable interactions between the cell housing 12 and any substances flowing therethrough.

For example, it has been found that certain materials, such as PEEK, allow for improved ease of manufacture because features may be drilled to very precise tolerances with conventional machining tools. In contrast, manufacture of cell housings 12 with other materials, such as nylon, may be more difficult to perform because of a tendency for conventional drill bits to walk during drilling, creating dimensional error, thus requiring more precisely controllable machining tools. Nonetheless, the particular application for the flow cell 10 may make certain types of materials more desirable. Thus, it should be understood that, while certain materials, such as PEEK, are desirable due to the ease of manufacture associated therewith, appropriate manufacturing techniques may be selected to allow the use of any desired material, including, but not limited to, nylon, fluoro-polymers, stainless steel, and other metals.

An illumination optical fiber 22 is inserted in the illumination port 14. A detection fiber 24 is inserted in the detection port 16. A fluid inlet conduit 26 is inserted in the fluid inlet port 18. A fluid outlet conduit 28 is inserted in the fluid outlet port 20. The fibers 22, 24 and conduits 26, 28 may be affixed in place using an adhesive 25, such as epoxy, glue, or another suitable type. The fibers 22, 24 and conduits 26, 28 are positioned so as to bound portions of a detection chamber 30 without requiring further optical windows (which could be added if desired). Notably, the ports 14, 16, 18, 20 are sized so that the fibers 22, 24 and conduits 26, 28, together with the adhesive 25, create substantially fluid-tight seals that prevent the escape of fluids from the detection chamber 30 (except, of course, as intended through the fluid outlet conduit 28).

In one example, the ports 14, 16, 18, 20 had diameters of fifteen mils (about 380 microns), the conduits 26, 28 were made with 14.2 mil (about 360 micron) PEEK tubing, and the fibers 22, 24 were made with approximately 14 mil (about 355 micron) bare optical fiber. In this example, a satisfactory seal was accomplished using high-grade epoxy. The conduits may be made of any suitable material including, but not limited to, polyimide-coated fused silica or PEEK. The optical fibers may be made from any suitable material including, but not limited to, polyimide-coated fused silica, aluminum-coated silica, or bare fused silica.

In operation, an analyte stream enters the detection chamber 30 through the inlet conduit 26, travels through the detection chamber 30, and exits the detection chamber 30 through the outlet conduit 28. An illumination source 32 provides the desired optical signal through the illumination optical fiber 22. The optical signal passes through the detection chamber 30 (as indicated by arrow 34) and is received by the detector optical fiber 24, which carries the signal to a detector 36 for analysis. Notably, the optical path through the detection chamber 30 is coaxial with the flow of the analyte through the detection chamber 30—thus creating an optical path length equal to the length of the detection chamber 30. It will be readily apparent to one skilled in the art that the length of the detection chamber 30 may be varied to provide an optical path length optimized to provide the desired signal properties.

Figure 2C:
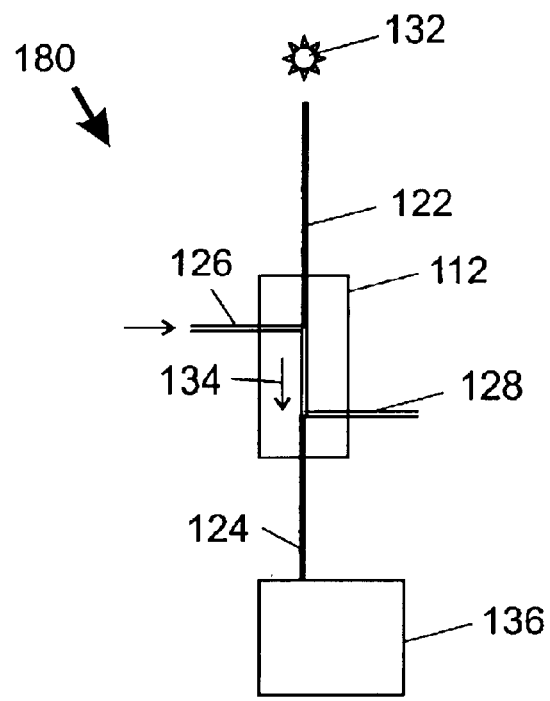
FIG. 2C is a block diagram of an optical detection system including the optical detection flow cell of FIG. 2A.

In another embodiment, shown in FIGS. 2A–2C, an optical detection flow cell 100 includes fittings 102–105 that may be used in lieu of epoxy to simplify assembly, disassembly, and/or repair of the device 100. For example, an optical detection flow cell 100 according to such an embodiment includes a monolithic cell housing 112, an illumination port 114, a detection port 116, a fluid inlet port 118, and a fluid outlet port 120. The cell housing 112 may be made from a block of any suitable material, including, but not limited to, metals, such as aluminum or stainless steel; glasses; and polymers, such as poly(ether ether ketone) (PEEK) or polyimide. It will be readily apparent to one skilled in the art that the material may be selected to simplify manufacturing and/or minimize undesirable interactions between the cell housing 112 and any substances flowing therethrough.

An illumination optical fiber 122 is inserted in the illumination port 114. A detection fiber 124 is inserted in the detector port 116. A fluid inlet conduit 126 is inserted in the fluid inlet port 118. A fluid outlet conduit 128 is inserted in the fluid outlet port 120. The fibers 122, 124 and conduits 126, 128 are held in place using conventional #6–32 threaded fittings or any other suitable fitting (consequently, the ports 114, 116, 118, 120 will be sized appropriately to accommodate the selected fittings 102–105). The fibers 122, 124 and conduits 126, 28 are positioned so as to bound portions of a detection chamber 130. Notably, the ports 114, 116, 118, 120 have tapered portions 151–153 to accept the tip of a #6–32 threaded fitting to create substantially fluid-tight seals to prevent the escape of fluids from the detection chamber 130 (except, of course, as intended through the fluid outlet conduit 128). The fibers 122, 124 and conduits 126, 128 are inserted in the fittings 102–105 and extend just past the tip of the fittings 102–105 into a cylindrical portion 161–163 of the ports 114, 116, 118, 120 to bound portions of the detection chamber 130. It should be noted that the flow cell 10, described above with respect to FIG. 1, may be fabricated using fittings, such as the fittings 102–105, in lieu of the adhesive 25, thus providing the same benefits as those achieved by the flow cell 100 shown in FIGS. 2A–2C.

To properly position the fibers 122, 124 and conduits 126, 128 within the cell housing 112, a spacing fiber (not shown) may be inserted into a port 114, 116, 118, 120 adjacent to the port into which the fiber 122, 124 or conduit 126, 128 is to be positioned and the spacing fiber extended a sufficient distance to occlude that port. The spacing fiber should be smaller in diameter than either of the fibers 122, 124 or conduits 126, 128, typically by about half. The fiber 122, 124 or conduit 126, 128 to be positioned is then inserted into the desired port until it contacts the spacing fiber. Because the spacing fiber is smaller in diameter, the inserted fiber 122, 124 or conduit 126, 128 protrudes partially into the detection chamber 130. Thus, when the spacing fiber is removed and a fiber 122, 124 or conduit 126, 128 is positioned in its place, the newly inserted fiber 122, 124 or conduit 126, 128 will be blocked by the protruding end of the previously positioned fiber 122, 124 or conduit 126, 128. As a consequence, each fiber 122, 124 or conduit 126, 128 is positioned within the detection chamber 130, but only protrudes partially therein, thus allowing fluid flow through the detection chamber 130. Alternatively, a fiber 122, 124 or conduit 126, 128 may be positioned mechanically with an instrument having sufficient precision to allow a measured amount of fiber 122, 124 or conduit 126, 128 to be inserted into the flow cell 100. Also, optical fibers, X-ray, CAT scans or other non-destructive techniques may be used to observe the progress of the fiber 122, 124 or conduit 126, 128 within the flow cell 112 to permit precise positioning therein.

FIG. 2C illustrates an optical detection system 180 including the flow cell 100. Referring to FIGS. 2A–2C, in operation, an analyte stream enters the detection chamber 130 through the inlet conduit 126, travels through the detection chamber 130, and exits the detection chamber 130 through the outlet conduit 128. An illumination source 132 provides the desired optical signal through the illumination optical fiber 122. The optical signal passes through the detection chamber (as indicated by arrow 134) and is received by the detector optical fiber 124, which carries the signal to a detector 136 for analysis. Notably, the optical path through the detection chamber 130 is coaxial with the flow of the analyte through the detection chamber 130—thus creating an optical path length equal to the length of the detection chamber 130. It will be readily apparent to one skilled in the art that the length of the detection chamber 130 may be varied to provide an optical path length optimized to provide the desired signal properties.

Referring to FIGS. 3A–3B, an optical detection flow cell 200 according to another embodiment may include multiple detection chambers 230A–230N so that a plurality of analyte streams may be analyzed in parallel. (Although FIGS. 3A–3B show the device 200 having eight detection chambers 230A–230N, it will be readily apparent to one skilled in the art that any number of chambers 230A–230N may be provided. For this reason, the designation "N" is used to represent the last column 230N, with the understanding that "N" represents a variable and could represent any desired number of columns. This convention is used throughout this document.) Thus, the flow cell 200 comprises a monolithic cell housing 212 with illumination ports 214A–214N, detection ports 216A–216N, fluid inlet ports 218A–218N, and fluid outlet ports 220N—220N. The flow cell 200 and each detection chamber 230A–230N provided therein is constructed and operated in the same manner as described above with respect to the flow cell 100.

Figure 4C:
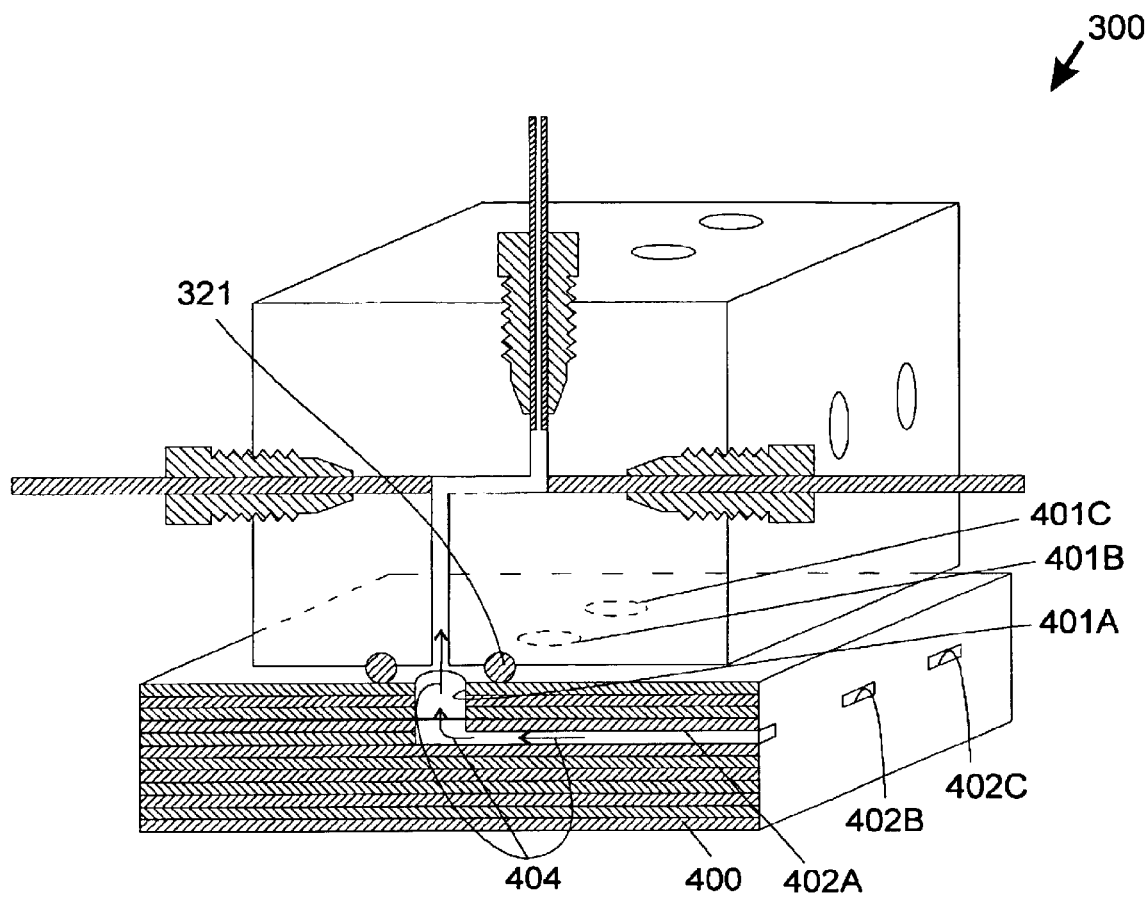
FIG. 4C is a cross-sectional, perspective view of the optical detection flow cell of FIG. 4A forming a press-fit seal with a microfluidic device.

In another embodiment, shown in FIGS. 4A–4C, a flow cell 300 includes a monolithic cell housing 312, an illumination port 314, a detection port 316, a fluid inlet port 318, a fluid outlet port 320, and a seal 321. An illumination optical fiber 322 is inserted in the illumination source port 314. A detection fiber 324 is inserted in the detector port 316. A fluid outlet conduit 328 is inserted in the fluid outlet port 320. The fibers 322, 324 and conduit 328 are held in place using conventional #6–32 threaded fittings or any other suitable fitting (consequently, the ports 314, 316, 320 will be sized appropriately to accommodate the selected fittings 302–304). The fibers 322, 324 and conduit 328 are positioned so as to bound portions of a detection chamber 330. The components and fittings of the flow cell 300 may be made from the same materials and assembled using the same process as described above. The seal 321 is preferably an O-ring made of silicon, ethylene propylene diene monomer (EPDM), perfluoroelastomers, or any other suitable material that may be selected as appropriate for particular substances anticipated to be used with the flow cell 300. The O-ring 321 is seated in an annular groove 323 and surrounds a central protrusion 325.

As shown in FIG. 4C, the O-ring 321 forms a press-fit fluidic interface that allows the flow cell 300 to be pressed directly against a microfluidic device 400 to provide a substantially fluid-tight seal to allow a fluid flowing through a channel 402A–402C (as indicated by arrows 404) to pass from the microfluidic device 400 into the flow cell 300. The microfluidic device 400 may be any device that provides a fluidic output for which optical analysis is desired. For example, but without limitation, the microfluidic device may be a chromatographic separation device, an assay device, or a well-plate. The microfluidic device 400 may provide multiple fluidic outputs 401A–401N simultaneously, which may be accommodated if multiple detection chambers are provided, such as by the flow cell 200 described above with reference to FIGS. 3A–3B or the flow cell 500 described below with reference to FIG. 4D. For example, the microfluidic device 400 may be a multi-column, high throughput chromatography device (or "chip.")

When the flow cell 300 is pressed against the microfluidic device 400, the O-ring 321 is compressed, forming the desired seal. The tip of the central protrusion 325 preferably does not contact the surface of the microfluidic device 400 (and may be recessed slightly from the plane of the lower surface of the flow cell 300). The central protrusion 325 acts to retain the O-ring 321, thus obviating the need for adhesives or other bonding methods. Also, the central protrusion 325 prevents the O-ring 321 from deforming inwardly towards the outlet of the microfluidic device 400, thereby preventing any inadvertent or undesirable occlusion of the outlet by the O-ring 321. This interface design also minimizes the amount of dead volume between the flow cell 300 and the microfluidic device 400 because the central protrusion 325 acts to occupy some or all of the volume between the flow cell 300 and the microfluidic device 400 and bounded by the O-ring 321.

Figure 4D:
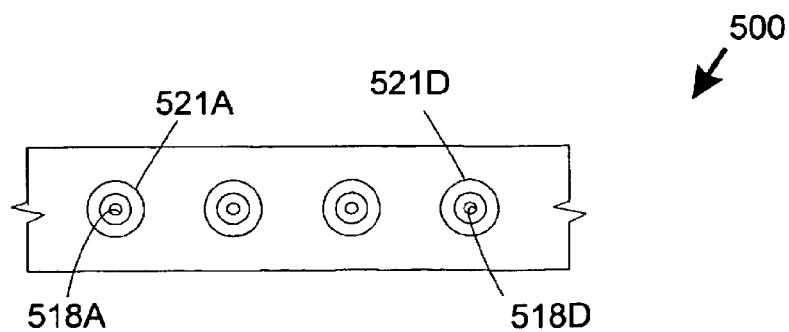
FIG. 4D is a partial bottom view of a portion an alternate embodiment of the optical detection flow cell of FIG. 4A.

As shown in FIG. 4D, such an interface approach may be used with a flow cell 500 having multiple inlet ports 518A–518D using multiple O-rings 521A–521D. While only four such inlets ports 518A–518D are shown, it will be readily understood by one skilled in the art that any number of inlet ports may be provided. Also, the O-rings 521A–521D may be incorporated or substituted with a single gasket having either a series of interconnected O-rings or a sheet gasket with raised O-ring segments.

The flow cell 300 shown in FIGS. 4A–4D is operated in the same fashion as the other embodiments described above, except that the flow cell 300 is placed adjacent to and pressed against the microfluidic device 400 to form an interface therebetween. In this manner, fittings between the microfluidic device 400, conduits between the microfluidic device 400 and the flow cell 300, and fittings between conduits and the flow cell 300 are eliminated, thereby reducing the number of components that must be assembled and maintained during fabrication and operation of the flow cell 300.

One significant advantage provided by the invention, as illustrated by the embodiments disclosed herein, is that the channel housing of the flow cell may be manufactured from a single block of a selected material. This is because the arrangement of the ports allows all of the internal structures to be formed by drilling or boring into a monolithic block to form the ports and the detection chamber. Thus, no assembly of the channel housing is required, minimizing fabrication steps.

Also, the use of conventional fluid-tight fittings allows for the simple and efficient connection of the desired conduits and fibers. Furthermore, use of conventionally available polyimide-coated fused silica conduits and fibers allows use of identical fittings for both as both have the same diameter of about 360 microns (14.2 mil). Moreover, because the fibers form boundaries of the detection chamber, no additional window or intervening structure is required, ensuring that substantially all of the frequency spectrum carried by the fiber can be delivered to the analyte and received by the detector. Consequently, the need for optically transparent structural components and the attendant compatibility and bonding issues are obviated.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. An optical analysis flow cell comprising:
    a monolithic cell housing that defines
        a detection chamber having a first end, a second end, and a central axis;
        a fluid inlet port in fluid communication with the detection chamber;
        a fluid outlet port in fluid communication with the detection chamber;
        an illumination port in fluid communication with the detection chamber;
        a detection port in fluid communication with the detection chamber;
        wherein the illumination port is positioned at the first end and the detection port is positioned at the second end so that an optical path between the illumination port and the detection port traverses substantially all of the central axis; and
    a first optical fiber having a distal end, wherein the distal end of the first optical fiber is positioned within the illumination port.

2. The optical analysis flow cell of claim 1 wherein the monolithic cell housing comprises a polymer.

3. The optical analysis flow cell of claim 2 wherein the polymer comprises poly(ether ether ketone).

4. The optical analysis flow cell of claim 2 wherein the polymer comprises polyimide.

5. The optical analysis flow cell of claim 1 wherein any of the fluid inlet port, fluid outlet port, illumination port, and detection port are adapted to receive a fitting.

6. The optical analysis flow cell of claim 5 wherein the fitting is a threaded fitting.

7. The optical analysis flow cell of claim 1 further comprising a second optical fibers having a distal end, wherein the distal end of the second optical fibers is positioned within the detection port.

8. The optical analysis flow cell of claim 7 wherein the first and second optical fibers comprise polyimide-coated fused silica.

9. The optical analysis flow cell of claim 7 wherein the first and second optical fibers comprise fused silica.

10. The optical analysis flow cell of claim 1 wherein the fluid inlet port and fluid outlet port are adapted to permit positioning of fluid conduits.

11. The optical analysis flow cell of claim 10 wherein the fluid conduits comprise polyimide-coated fused silica.

12. The optical analysis flow cell of claim 10 wherein the fluid conduits comprise poly(ether ether ketone).

13. The optical analysis flow cell of claim 1, further comprising an O-ring affixed to the monolithic cell housing around the fluid inlet port.

14. An optical analysis flow cell comprising:
    a monolithic cell housing;
    a fluid inlet conduit sealingly affixed to and partially penetrating the monolithic cell housing, the fluid inlet conduit having an inner diameter;
    a fluid outlet conduit sealingly affixed to and partially penetrating the monolithic cell housing, the fluid outlet conduit having an inner diameter and the fluid outlet conduit being in fluid communication with the fluid inlet conduit;
    an illumination optical fiber sealingly affixed to and partially penetrating the monolithic cell housing, the illumination optical fiber being in fluid communication with the fluid inlet conduit and the fluid outlet conduit; and
    a detection optical fiber sealingly affixed to and partially penetrating the monolithic cell housing, the detection optical fiber being in fluid communication with the fluid inlet conduit, the fluid outlet conduit, and the illumination optical fiber; wherein the illumination optical fiber and the detection optical fiber are in sensory communication over an optical path length that is substantially longer than the inner diameter of the fluid inlet conduit and substantially longer than the inner diameter of the fluid outlet conduit.

15. The optical analysis flow cell of claim 14 wherein the monolithic cell housing comprises a polymer.

16. The optical analysis flow cell of claim 15 wherein the polymer comprises poly(ether ether ketone).

17. The optical analysis flow cell of claim 15 wherein the polymer comprises polyimide.

18. The optical analysis flow cell of claim 14 wherein any of the illumination optical fiber and the detection optical fiber comprise polyimide-coated fused silica.

19. The optical analysis flow cell of claim 14 wherein any of the illumination optical fiber and the detection optical fiber comprise fused silica.

20. The optical analysis flow cell of claim 14 wherein any of the fluid inlet conduit and the fluid outlet conduit comprise polyimide-coated fused silica.

21. The optical analysis flow cell of claim 14 wherein any of the fluid inlet conduit and the fluid outlet conduit comprise poly(ether ether ketone).

22. An optical analysis flow cell comprising:
   a monolithic cell housing defining a fluid flow channel having an orthogonal detection region, the orthogonal detection region having a detection axis;
   an optical signal fiber in sensory and fluid communication with the orthogonal detection region; and
   an optical detection fiber in sensory and fluid communication with the optical signal source across the detection axis;
   wherein the optical signal fiber and the optical detection fiber are adapted to create a substantially fluid tight seal with the orthogonal detection region.

23. The optical analysis flow cell of claim 22, further comprising a fitting associated with any of the optical signal fiber and the optical detection fiber.

24. The optical analysis flow cell of claim 22 wherein the monolithic cell housing comprises a polymer.

25. The optical analysis flow cell of claim 24 wherein the polymer comprises poly(ether ether ketone).

26. The optical analysis flow cell of claim 24 wherein the polymer comprises polyimide.

27. The optical analysis flow cell of claim 22 wherein any of the optical signal fiber and the optical detection fiber comprise polyimide-coated fused silica.

28. The optical analysis flow cell of claim 22 wherein any of the optical signal fiber and the optical detection fiber comprise fused silica.

29. A system for performing optical analysis of a fluid sample, the system comprising:
   a monolithic flow cell housing defining a plurality of flow cell and a plurality of inlet ports, wherein each inlet port of the plurality of inlet ports corresponds to a flow cell of the plurality of flow cells;
   a microfluidic device having a plurality of outlet ports
   wherein the each inlet port of the plurality of inlet ports of the monolithic flow cell housing adapted to form a press-fit seal with a corresponding outlet port of the plurality of outlet posts of the microfluidic device.

30. The system of claim 29 wherein each flow cell of the plurality of flow cells defines an orthrogonal detection region.

31. The system of claim 29, further comprising an optical detection instrument in sensory communication with each flow cell of the plurity of flow cells.

32. The system of claim 29 wherein the microfluidic device comprises a plurality of separation columns adapted to perform liquid chromatography.

* * * * *